United States Patent [19]

Koblitz et al.

[11] Patent Number: 4,504,231

[45] Date of Patent: Mar. 12, 1985

[54] PROCESS FOR FILLING TEETH

[75] Inventors: Francis F. Koblitz, York; Jane L. Reichart, Hanover, both of Pa.

[73] Assignee: Dentsply Research & Development Corp., Milford, Del.

[21] Appl. No.: 470,177

[22] Filed: Apr. 11, 1983

Related U.S. Application Data

[63] Continuation of Ser. No. 233,951, Feb. 17, 1981, abandoned.

[51] Int. Cl.³ ............................................... A61K 6/08
[52] U.S. Cl. ............................... 433/228; 204/159.13; 260/998.11; 523/116; 523/117; 433/226
[58] Field of Search ...................... 204/159.13, 159.22; 528/24, 21, 12; 526/279; 523/116, 117; 260/998.11; 433/226, 228

[56] References Cited

U.S. PATENT DOCUMENTS

| 3,084,436 | 4/1963 | Landry | 260/998.11 |
| 3,835,090 | 9/1974 | Gander et al. | 260/998.11 |
| 4,308,014 | 12/1981 | Kawahara et al. | 260/998.11 |
| 4,323,348 | 4/1982 | Schmitz-Josten et al. | 260/998.11 |
| 4,383,826 | 5/1983 | Butler et al. | 523/116 |

Primary Examiner—Lorenzo B. Hayes
Attorney, Agent, or Firm—Woodcock Washburn Kurtz Mackiewicz & Norris

[57] ABSTRACT

Process for filling dental cavities with radiation curable silaneous adhesives comprising a polymerizable resin comprising at least 20% by weight of a polymerizable silane and optionally up to about 80% by weight of a polymerizable, ethylenically unsaturated material. According to a preferred embodiment, the polymerizable silane is either an acrylosilane or a vinyl silane.

6 Claims, No Drawings

PROCESS FOR FILLING TEETH

This is a continuation of application Ser. No. 233,951, filed Feb. 17, 1981, now abandoned.

BACKGROUND OF THE INVENTION

1. Field of the Invention

This invention concerns adhesive formulations and related methods of adhesion involving the use of materials sensitive to radiation. More particularly, this invention relates to adhesives which are adapted to being cured or set on demand by application of radiant energy, especially visible or ultraviolet light. Such adhesives are formulated employing a major proportion of certain silane species. Optionally, these formulations may contain non-silaneous polymerizable ethylenically unsaturated materials such as acrylic species. According to a preferred embodiment, such adhesives may be used for various adhesive applications in dentistry.

It has been desired to employ as adhesives formulations which are suitable for use in "demand settable" adhesive processes. Such a process would employ adhesives which do not begin to cure or harden until a preselected point in time and then are set in a relatively short period of time after curing is initiated.

It has also been desired to employ certain silane species in adhesive formulations. Such employment of silanes has been thought to lend certain beneficial properties to the adhesives thus constituted. Accordingly, such adhesives are believed to be relatively impervious to water and to coat surfaces to be joined in a desirably uniform manner. For certain adhesive uses, it is desirable to employ adhesives which are not easily degraded by heat. In typical commercial adhesives, the application of high temperatures tends to cause thermal breakdown of the compositions with concomitant loss of physical and chemical properties and liberation of noxious odors. At present, only a limited number of adhesives, such as the zinc and other metal phosphates, and certain epoxy and phenolic resins are well adapted for resistance to thermal degradation; none of these is demand settable.

2. Description of the Prior Art

It has been known to employ certain silanes in polymerizable compositions including radiation polymerizable compositions. Such employment has usually been for the purpose of securing good bonding of resin matrices with fillers or with substrates. Silanes have also been employed for viscosity modification of resin systems. The usual mode of polymerization of silanes in polymerizable resins is thermal; radical inhibitors are frequently included to prevent premature thermal polymerization. It has not been known to employ silanes as principal constituents of actinic light polymerization compositions; it has generally been thought that photopolymerization of such resins would proceed sluggishly. Use of silanes as polymerizable constituents of demand set adhesives has been, accordingly, unknown.

OBJECTS OF THE INVENTION

It is an object of this invention to provide adhesive formulations which are demand settable. It is another object to provide such adhesives which comprise silane species in major proportion. Yet another object is to furnish adhesives which are capable of withstanding elevated temperatures without substantial degradation, loss of physical properties and liberation of noxious odors. It is also desired that the adhesives of this invention be relatively impervious to water and to demonstrate good coating of substrates. Another object is to provide such compositions which are suitable for industrial assembly processes such as fixturing. A further object is to provide adhesion processes employing such materials. A particular object is to develop such processes which are adaptable for use in dentistry. These and other objects are accomplished through the employment of one or more embodiments of the present invention.

SUMMARY OF THE INVENTION

It has been discovered that demand settable adhesives may be formulated employing certain silane species together with a photosensitizing system. Such adhesives may be set on demand by the application of suitable actinic light radiation. Such adhesives are water resistant, exhibit good substrate coverage, and show improved resistance to degradation at elevated temperatures. These adhesives comprise a polymerizable resin comprising at least about 20% by weight of at least one light polymerizable silane. Other ethylenically unsaturated polymerizable species may also be included such as acrylates, methacrylates, and vinyl compounds. The adhesives may, optionally, be filled. The photosensitizing system may preferably comprise an alpha diketone and an amine. Depending upon the radiation sensitizing system thus chosen, these adhesive formulations will polymerize when they are exposed to the appropriate radiation, such as visible light. In certain embodiments, it has been found desirable to supplement the photosensitizing system with a peroxide or other polymerization promoting species to facilitate the rapid polymerization and setting of the adhesives.

DETAILED DESCRIPTION OF THE INVENTION

The adhesive compositions of this invention comprise polymerizable resins comprising at least 20% by weight of certain polymerizable silane and related species, up to 80% by weight of a polymerizable ethylenically unsaturated material and an amount of a photosensitizing system effective to cause polymerization of the adhesive when it is exposed to actinic light. Such adhesives may also comprise organic or inorganic fillers and other modificants.

The silanes which are suitable for use in the practice of this invention are any of those silanes which contain functionalities which participate in photochemical polymerization. In general, such silanes have one or more reactive ethylenic unsaturations. Such unsaturations include, for example, vinyl, allyl, "dienyl", acetylenyl, acrylyl, methacrylyl, other acrylic homologs, and many other reactive ethylenic functionalities. Preferably, such silanes belong to the class of acrylosilanes, which class includes methacrylic and homologous species. Such families may be represented by the formula:

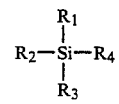

I.

where $R_1$–$R_4$ are the same or different and may be H, alkyl, alkenyl, aryl, aralkyl, alkaryl, alkoxy, vinyl, aryloxy, acyloxy etc. having from 1 to about 30 carbon atoms and where at least one of $R_1$-$R_4$ is alkyl, aryl, aralkyl, alkaryl having from 1 to about 30 carbon atoms and being substituted with at least one group having formula II:

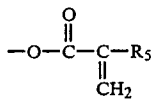

where $R_5$ is H, alkyl, alkenyl or phenyl having from 1 to about 6 carbon atoms. Of these acrylosilanes, preferred species include those where $R_1$-$R_3$ are the same or different and may be methoxy, ethoxy, propoxy, etc., methoxyethoxy, butoxyethoxy, etc., methyl, ethyl, propyl, etc., and where $R_4$ may be acryloxyethyl, acryloxypropyl, methacryloxypropyl, methacryloxybutyl, etc. Those skilled in the art will appreciate that pluralities of such acrylic substituents may be appended to $R_4$ and that others of the substituents on silicon, i.e. $R_1$-$R_3$, may also be so substituted. Species such as 3-methacryloxypropyltrimethoxysilane and methacryloxypropyltris(methoxyethoxy)silane have been found to be most preferred for use in certain embodiments of this invention.

Another family of silane species which is useful in the practice of this invention include those light polymerization silanes which have non-acrylic photochemically reactive ethylenic unsaturations. Accordingly, such family may be represented by formula I:

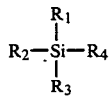

where $R_1$-$R_4$ have the meanings suscribed to them previously and at least one of $R_1$-$R_4$ has the formula:

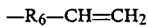

where $R_6$ is alkyl, aryl, aralkyl, or alkaryl having from 1 to about 30 carbon atoms. While formula III discloses a terminal ethylenic unsaturation, those skilled in the art will easily recognize that compounds having internal ethylenic unsaturations may also be suitable for the practice of one or more embodiments of the present invention. This family will be recognized to include vinyl, allyl, and other ethylenically unsaturated silanes. It should be appreciated that others of groups $R_1$-$R_3$ may also include one or more of such reactive ethylenic unsaturations.

Exemplary members of this family of polymerizable silanes which is useful for the practice of the invention include, for example, allyldimethylsilane, allyltriethoxysilane, allyltrimethylsilane, diphenylvinylethoxysilane, divinyldiethoxysilane, phenylmethylvinylsilane, tetraallyloxysilane, tetravinylsilane, trimethylsilylacetylene, 1-(trimethylsilyl)propyne, trivinylethoxysilane, trivinylmethylsilane, vinyldimethylethoxysilane, vinylmethyldiacetoxysilane, vinylmethyl-diethoxysilane, vinyloxytrimethylsilane, vinyltriacetoxysilane, vinyltriethoxysilane, vinyltriisopropoxysilane, vinyltrimethoxysilane, vinyltrimethylsilane, vinyltriphenoxysilane, vinyltris(2-methoxyethoxy)silane, and related species.

Those skilled in the art will recognize that the above descriptions of silaneous materials suitable for use in the practice of one or more embodiments of this invention is, of necessity, limited. Those skilled in the art will understand that numerous ethylenically unsaturated silane compounds exist which are photochemically polymerizable. Such persons will easily be able to ascertain which of such compounds are suitable for inclusion in one or more embodiments of the invention. Accordingly, all such compounds may, prima facie, be used therein. Furthermore, mixtures of two or more of such silane compounds may be so employed.

Since most silane compositions available commercially have been treated with one or more inhibitors to suppress autopolymerization during storage, and since such inhibitors have been found to retard or prevent rapid photopolymerization, it may be necessary to remove most or all of such inhibitors from silane species for use in the practice of this invention.

The polymerizable resins useful for the formulation of the polymerizable adhesives of this invention preferably comprise at least 20% by weight of at least one of the silanes which have been described hereinabove. Alternatively, it is possible for such resins to comprise up to 100% of such silanes as well. Accordingly, amounts of silane varying from about 20% to about 100% by weight are preferred. More preferred are resins employing from about 40% to about 95% by weight of such silanes. Even more preferred are resins having from about 60% to about 90% of such silanes.

It has been found to be especially preferred to employ amounts of silane in the adhesives of this invention which are greater than about 50% by weight. Such adhesives exhibit particularly good physical properties at elevated temperatures. It is even more preferred to employ from about 60% to about 90% of such silanes for high temperature fixturing and other uses.

The polymerizable resins used to formulate the polymerizable adhesives of this invention may, in addition to the silane species, also contain up to about 80% of a poymerizable, ethylenically unsaturated material which does not contain silicon. Thus, from 0% to about 80%, and preferably from about 5% to about 60% of such ethylenically unsaturated, polymerizable materials may be added. It is even more preferred to employ from about 10% to about 40% of such compounds. Preferred reactive, ethylenically unsaturated materials for the practice of this invention include the acrylic, methacrylic, ethacrylic, etc. esters of various alcohols and other hydroxyl containing polymers and prepolymers. Also useful, are vinyl, allyl, styryl, "enyl", "dienyl", acetylenyl, and numerous other reactive, ethylenically unsaturated species. Preferred for use for the practice of the invention are the acrylic and lower alkyl acrylic acid esters, such as the acrylates and methacrylates. Exemplary species of this class include the acrylic, methacrylic, etc. esters of materials having from 1 to about 40 and preferably from 1 to about 30 carbon atoms. Such materials may be substituted with, inter alia, hydroxyl, amino, thiol, halogen, and other functionalities. Especially preferred examples include the esters of methyl-, ethyl-, isopropyl-, perfluorooctyl-, hydroxyethyl-, 4-hydroxyphenyl-, aminoethyl-, aminophenyl-, thiophenyl-, and numerous other alcohols. Preferred among these are the acrylic, methacrylic, etc. esters of bisphenol-A and its epoxy resins, prepolymers and related materials. The acrylic esters of 2,2-bis(4-hydroxy-2,3,5,6tetrafluorophenyl)propane are also preferred. Those skilled in the art will recognize that numerous other species are also suitable. Polymerizable, ethylenically unsaturated materials having two or more reactive functionalities may also be included. Thus, di-, tri-, and other polyfunctional, ethylenically reactive species may be employed.

The polymerizable adhesives of this invention also comprise an amount of a photosensitizing system effective to cause polymerization of the adhesive when it is exposed to actinic light. The photosensitizing system may comprise any of those compounds which are capable of initiating such photopolymerization. Thus, the photosensitizing system may comprise sensitizing species for visible, ultraviolet, or other actinic light. For the practice of some embodiments of the invention, such photosensitizing system comprises an alpha diketone together with an amine. Such alpha diketones (also known as alpha-beta diketones) may be any of those alpha diketones capable of initiating photopolymerization in the polymerizable adhesive systems of this invention. Of these, camphoroquinone, benzil, biacetyl, 9,10-phenanthrenequinone, and 1,2-naphthoquinone have been found to be preferred. Most preferred is camphoroquinone. Numerous amines have been found to be useful when joined with alpha diketones in photosensitizing systems. Such amines as tributylamine, tripropylamine, etc. may be employed. Preferred species include the substituted amines such as N,N-dialkylalkanolamines, N-alkyldialkanolamines and trialkanolamines. N-methyldiethanolamine and N,N-dimethylethanolamine are most preferred. Such combinations of alpha diketones and amines to form photosensitizing systems will be recognized by those skilled in the art to be especially preferred for use in photopolymerizable adhesives which are to be polymerized by visible light.

The adhesives of this invention may also be polymerized by ultraviolet light. For such ultraviolet light polymerization, ultraviolet light sensitizing systems should be included. Those skilled in the art will recognize that numerous ultraviolet light sensitizing systems are known including numerous aromatic, ketonic and other families of compounds. One such family is represented by the formula:

IV.

where $R_7$ and $R_8$ may be the same or different and may be alkyl or aryl. Other sensitizers include benzoin alkyl ethers, which are preferred. Thus, the methyl, ethyl, propyl, etc. benzoic ethers may be employed. Benzoin methyl, ethyl, and isopropyl ethers have been found to be preferred. Also preferred, are benzoin ketals such as benzoin dimethylketal and analogous species. These may also be considered to be benzoin alkyl ethers.

According to certain embodiments of this invention, the photosensitizing system may comprise mixtures of ultraviolet and visible light sensitizing systems. Thus, for example, an alpha diketone and amine may be combined with a benzoin ether to form a broad spectrum photosensitizing system. Light polymerizable adhesives employing such sensitizing systems will have concomitantly broad polymerization response to light. Such combined photosensitizing systems are preferred in certain embodiments. It is believed that when benzoin alkyl ethers are combined with the alpha dione and amine to form such broad spectrum sensitizing systems in the adhesive formulations of the invention, the benzoin alkyl ethers are stabilized such that storage of the resulting polymerizable adhesives is facilitated. Accordingly, it is believed that it is possible to employ lesser quantities of benzoin alkyl ethers when such ethers are admixed with alpha diketones and amines than is otherwise required.

According to a preferred embodiment of this invention, the photosensitizing system is supplemented by the addition of a polymerization promoter. Such promoter may be of the type that those skilled in the art will recognize is frequently employed in thermal polymerization systems. Accordingly, such promoters may comprise peroxides and other radical reaction promoting compounds; peroxides have been found to be preferred. Peroxides which have been found to be preferred include benzoyl peroxide, di-tert-butyl peroxide and others. Accordingly, amounts of peroxide or other species which are effective to promote the polymerization of the polymerizable adhesives of the present invention may be included in the photopolymerization system. When included in the photosensitizing systems of the invention, the promoter species are added in an amount effective to increase substantially, the rate of the photopolymerization reaction. In general, promoters may be added in an amount of from about 0.1% to about 2% of the weight of the polymerizable resin.

The photosensitizing systems are present in the polymerizable adhesives of this invention in amounts effective to cause polymerization of the adhesive when the adhesive is exposed to actinic light of suitable wavelength and intensity. In general, such photosensitizing systems comprise from about 0.3% to about 8% of the total weight of the polymerizable adhesive. It is more preferred to employ such photosensitizing systems in amounts of from about 0.4 to about 6% of such total weight. Accordingly, in a typical polymerizable adhesive composition, the polymerizable resin comprises approximately 94% by weight of the total weight while the photosensitizing system comprises approximately 6% by weight of the total weight of the polymerizable adhesive. The individual constituents of the photopolymerization system may vary. Thus, camphoroquinone may be employed in the photosensitizing systems in amounts from about 0.1% to about 2% by weight of the total adhesive with from about 0.2% to about 1% being preferred. Accompanying the camphoroquinone may be an amine such as methyldiethanolamine. Such methyldiethanolamine may be added in amounts of from about 0.3% to about 6% by weight of the total weight of the polymerizable adhesive with from about 0.5% to about 3% being preferred. It has been found to be beneficial to admix, for example, benzoyl peroxide in such photosensitizing systems in amounts varying from about 0.1% to about 2% by weight of the total weight of the polymerizable adhesive. When ultraviolet light sensitizing systems are employed, such as benzoin ethers, they may, similarly, comprise from about 0.1% to about 6% by weight of the total weight of the polymerizable adhesive, with from about 0.3% to about 3% by weight being preferred. It should be appreciated that complex photosensitizing systems such as those which comprise in combination, alpha-diketones, amines, benzoin ethers, and peroxides may be formulated and that, in some embodiments, such complex, broad spectrum systems are preferred. Again, it should be appreciated that the best measure of the appropriate amount of components of a photosensitizing system according to the present invention is that amount which is effective in causing polymerization of the adhesive when such adhesive is exposed to actinic light.

Such polymerizable adhesives may also comprise inorganic fillers, organic fillers, pigments, colors, dyes, surface active agents, opacifiers, radioopaquing agents, and other modificants. Accordingly, it may be preferred in the practice of certain embodiments of this invention to admix the polymerizable adhesives of this invention with various amounts of fillers or other modificants. Thus, the adhesives may be admixed with fillers such as, for example, silica, quartz, etc. in weight ratios of up to about 1:6. It is frequently desirable to add fillers to the adhesives of this invention in amounts sufficient to render the compositions thixotropic so as to promote ease of handling and good physical properties. Accordingly, filled compositions may be formulated having up to about 80% by weight of filler or other modificant. Such filled or otherwise modified compositions are within the scope of this invention.

In general, the adhesives of this invention may be formulated by mixing together the selected components. Accordingly, it is generally necessary only to mix the silaneous species together with the non-silaneous polymerizable compounds (if any) and to add thereto the selected photosensitizing systems, along with the optional fillers, pigments, and other modificants. Thereafter, it is usually helpful to degas the formulation and/or to allow the formulation to stand for from about 6 hours to about 7 days to allow full homogenization and dispersion of the components of the mixture. Although these adhesives are light curable, preparation and storage away from incidental light is usually not necessary due to their remarkable stability to low ambient light levels. In use, the materials of this invention are simply dispensed as desired and exposed to light of the appropriate wavelength at a convenient, effective, intensity. Accordingly, either visible, ultraviolet or broad spectrum light, depending upon the photosensitizing system selected, is directed to the dispensed adhesive for a time sufficient to allow the adhesive to cure. This may be done using any convenient light source. Thus, a visible light curing unit, such as the Prisma-Lite TM, unit of the L. D. Caulk Co., may be used to expose visible light curable adhesives. The Caulk Nuva-Lite ® source may be used for ultraviolet polymerization of the adhesives of this invention having ultraviolet photosensitizing systems. In general, it is necessary only to expose the adhesives of this invention to relatively low levels of irradiation in order to secure polymerization. Thus, typical formulations may be exposed to a 0.4 watt/cm²/sec visible light for approximately 30 seconds to effect cures of up to about 6 millimeters in depth.

The adhesives of this invention are well adapted to industrial fixturing processes, and for other adhesive uses including uses in dentistry. Accordingly, such adhesives may be applied to a selection of articles to be "fixed" with respect to each other, the articles are then positioned as desired and the adhesive demand set to effect a rapid stabilization of the configuration of such articles. Such fixturing may be followed, optionally, by further configuration stabilization such as by application of additional adhesives, filling materials, or other compositions.

The adhesives of this invention are particularly suited for use in dentistry. Accordingly, they may be used in the construction and application of crowns and bridges, dental veneers, orthodontic appliances, and numerous other oral applications. The high water resistivity of such adhesives make them particularly suited for such uses. To practice the inventive process for filling teeth it is necessary only to apply the silaneous adhesives of the present invention, preferably those having substantial loadings of particulate, inorganic filler and exposing the adhesive to actinic light in a biologically compatible fashion. Most preferably, the ratio of resin to filler loadings of such materials are from about 1:2 to about 1:5.

The following examples are included by way of illustration only and are not to be construed as limiting.

EXAMPLE 1

A polymerizable resin was formulated by blending together the following constituents:

| | |
|---|---|
| Epocryl TM 370 (a glycidyl acrylate of bisphenol-A, Shell Co.) | 1.0 g |
| 3-methacryloxypropyltrimethoxysilane | 0.4 g |
| Vinyl-tris(methoxyethoxy)silane | 0.19 g |
| Benzoyl peroxide | 0.01 g |
| Camphoroquinone | 0.1 g |
| Methyl diethanolamine | 0.3 g |
| | 2.0 g |

The blend was allowed to stand in the dark for approximately 12 hours at which time a hazy-clear, fluid, uniform blend was evidenced. The blend was degased under vacuum several times and filled into a mold having a depth of 6.5 mm. The filled mold was exposed to light from a Caulk Prisma-Lite TM unit producing a spectrum of light of 400–500 mm with a power of 0.4 w/cm²/sec for 30 seconds. A complete, rubbery cure resulted which was uniform throughout the depth of the mold.

EXAMPLE 2

A treated, inorganic filler was prepared by mixing together 97.5 g of particulated quartz of size less than 100 mesh with 2.0 g of 3-methacryloxypropyltrimethoxysilane and 0.5 g of Dow-Corning silicone surfactant 193. This treated filler was allowed to stand until the quartz was no longer "dusty" at which time it was milled in a ball mill for approximately 1 hour.

6.5 g of the above-described filler was blended with a mixture of 2.0 g of the formulation of Example 1 and an optional quantity of a suspending agent such as 0.04 g of Aerosil TM R-972. An additional 2.0 g of the treated quartz filler could be added resulting a total of 8.5 g of filler in 10.54 g of total weight. This filled composition was repeatedly degased under vacuum and stored in the dark. Exposure to light from Prisma-Lite TM unit for approximately 10 seconds yielding curing to a depth of approximately 5 mm. Exposure for an additional 10 seconds yielded total curing depths of approximately 6 mm. This filled adhesive is especially suitable for use as a high temperature demand set adhesive.

EXAMPLE 3

A filled, restorative adhesive suitable for dental, industrial, and other uses was formulated as follows:

A silane resin was constituted from 20 g of Nupol TM 46-4005 (Freeman), which is a bis-GMA 79 g of 3-methacryloxypropyltrimethoxysilane, and 1 g of Dow-Corning silicone surfactant 193. 24.4 g of pyrogenic silica (Aerosil TM OX-50) was blended with 0.6 g of the foregoing silane resin to form a treated filler. An acrylic resin was formulated from 19.64 g of the hexamethylene diisocyanate adduct of bis-GMA, 0.04 g of camphoroquinone, 0.2 g of methyldiethanolamine, and 0.12 g of a benzoin dimethylketal (Irgacure 651 TM -Ciba-Geigy).

7.5 g of the treated filler was mixed with 3.2 g of the acrylic resin and 0.8 g of additional silane resin; the resulting blend was degased under vacuum. A 2 mm layer of this adhesive was polymerizable in air in approximately 10 seconds by exposure to light from a Caulk Prisma-Lite TM unit. While this polymerized layer exhibited a slightly tacky surface, it was easily polishable and substantial to the touch. This filled adhesive was employed to bond together two glass microscope slides. The bond thus formed was strong and resisted boiling water for at least 2 hours.

EXAMPLE 4

A silaneous resin could be prepared comprising 10 g of 3methacryloxypropyltrimethoxysilane from which nearly all inhibitor has been removed (electrical grade from Petrarch Co.), 0.1 g camphoroquinone and 0.3 g methyldiethanolamine. This silaneous resin was sluggishly curable employing a Prisma-Lite TM unit. When a filler composition such as silanated finely particulated quartz is added to this silaneous adhesive formulation, polymerization with visible light is facilitated. Accordingly, a 1:5 blend of resin and filler is easily curable with the Prisma-Lite TM unit and is suitable for use as a high temperature, water resistant adhesive composition.

EXAMPLE 5

The composition of Example 4 could be admixed with 0.2 g of benzoyl peroxide. This improved composition is readily photopolymerizable both with and without inorganic, particulate filler.

EXAMPLE 6

A filled, light curable adhesive composition was formulated as follows: 76 g of Epocryl TM 370 (Shell Chemical Co.) was mixed with 20 g of 3-methacryloxytrimethoxysilane (electrical grade-Petrarch), 3 g of N-methyldiethanolamine, and 1 g of camphoroquinone. 2 g of this resinous matrix was mixed with 0.1 g of colloidal silica (Syloid TM 63-X, W. R. Grace Co.) until uniform. 7.9 g of 400 mesh vitreous silica was then added to the partially filled resinous composition, blended until fully dispersed, and repeatedly degassed in vacuo. This material cures rapidly when exposed to visible light and may be used to adhere glass to glass, porcelain to porcelain, glass to porcelain, glass to steel, etc.

EXAMPLE 7

The composite adhesive of Example 6 was used to fill a prepared, human tooth. Thus, a human tooth was excavated in the traditional way, filled with the material of Example 6, and exposed for 20 seconds to visible light at an intensity of 400 mw/cm$^2$/sec. The material photopolymerized easily, filled the tooth cavity completely, and evidenced good resistance to aqueous fluids.

EXAMPLE 8

The effectiveness of photopolymerization promoters was demonstrated. A mixture of 60% Epocryl TM 370 and 40% 3-methacryloxypropyltrimethoxysilane was formulated. To this stock solution was added either nothing, 1% by weight copper II-ethylacetoacetate, 0.5% camphoroquinone, or 0.5% camphoroquinone and 1% copper ethylacetoacetate. Each of the materials was exposed to light from a Caulk Prisma-Lite TM unit and the results recorded. Both the unmodified resin mixture and the resin mixture having the copper compound did not polymerize after 60 seconds of exposure from the light. The mixture having only camphoroquinone gelled sluggishly yielding a tender, gelatinous polymerizate. The composition having both the camphoroquinone and copper polymerization promoter gelled rapidly and completely demonstrating a tough polymerizate. Accordingly, species such as copper II ethylacetoacetate may replace amine species such as methyldiethanolamine in the visible light curable silaneous adhesives of the present invention.

EXAMPLE 9

A high temperature, photocurable adhesive resin composition was formulated from the following constituents:

| | |
|---|---|
| methacryloxypropyltrimethoxysilane (electronic grade) | 113 g |
| Epocryl TM 370 acrylic species (Shell Co.) | 80 g |
| camphoroquinone | 1 g |
| N—methyldiethanolamine | 2 g |
| vinyltris(methoxyethoxy)silane | 3.8 g |
| benzoyl peroxide | 0.2 g |
| copper II ethylacetoacetate | 1 g |
| Dow-Corning 193 silicone surfactant | 1 g |
| Irgacure TM 651 (benzoin dimethylketal) | 1 g |
| | 203 g |

This unfilled material polymerized to a depth of approximately 7.0 mm after exposure for 20 seconds to light from a Caulk Prisma-Lite TM unit.

EXAMPLE 10

10 g of the composition of Example 9 were mixed with 0.8 g of pyrogenic silica (Aerosil TM -972), and 40 g of microfine vitreous silica. This filled material polymerizes to a depth of approximately 4.3 mm after exposure to visible light from a Caulk Prisma-Lite TM unit. After a 20 second exposure to a 1.0 watt/cm$^2$/sec visible light source, polymerization to approximately 5.5 mm was evidenced. This filled composition was used for the fixturing of a lamp tube to its supporting sleeve, polymerizing the composition for 10 seconds with said 1 watt source. Operation of the lamp for approximately 45 minutes at 200° F. demonstrated that the adhesive continued to bond, generated no smoke, evidenced no odor, and showed little discoloration.

What is claimed is:

1. A process for filling teeth comprising
   applying to a prepared tooth cavity a light polymerizable adhesive comprising
   a polymerizable resin composition comprising
   (a) more than about 50% by weight of at least one silane having the formula

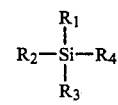

where $R_1$–$R_4$ are the same or different and are H, alkyl, alkenyl, aryl, aralkyl, alkaryl, alkoxy, vinyl, aryloxy, or acyloxy having from 1 to about 30 carbon atoms and where at least one of $R_1$–$R_4$ is alkyl, aryl, aralkyl or alkaryl having from 1 to about 30 carbon atoms and is substituted with at least one group having the formula $$-O-\underset{\underset{CH_2}{\|}}{\overset{\overset{O}{\|}}{C}}-C-R_5$$

where $R_5$ is H, alkyl or alkenyl having from 1 to about 6 carbon atoms, and (b) up to about 50% of a polymerizable ethylenically unsaturated material, and an amount of a photosensitizing system effective to cause polymerization of said adhesive when said adhesive is exposed to actinic light, and exposing said adhesive to actinic light for a time sufficient to harden said adhesive.

2. The process of claim 1 wherein said polymerization resin composition further comprises from about 0.5% to about 10% by weight of the resin of a material having the formula $$R_2-\underset{\underset{R_3}{|}}{\overset{\overset{R_1}{|}}{Si}}-R_6-CH=CH_2$$

where $R_6$ is alkyl, aryl, alkaryl or aralkyl having from 1 to about 30 carbon atoms and $R_1$-$R_3$ have the same meaning defined in claim 1.

3. The process of claim 2 wherein $R_1$-$R_3$ were alkoxy(alkoxy) groups.

4. The process of claim 1 further comprising an amount of particulate, inorganic filler sufficient to render said adhesive thixotropic.

5. The process of claim 1 wherein said photosensitizing system comprises at least on alpha diketone and an amine.

6. The process of claim 1 wherein said photosensitizing system comprises either a benzoin compound or a compound having the formula $$R_7-\underset{}{\overset{\overset{O}{\|}}{C}}-R_8$$

where $R_7$ and $R_8$ are the same or different and are alkyl or aryl.

* * * * *